United States Patent
Zhang et al.

(10) Patent No.: US 10,246,415 B2
(45) Date of Patent: Apr. 2, 2019

(54) PROCESS FOR PREPARING CARBAZOLES

(71) Applicant: Dow Global Technologies LLC, Midland, MI (US)

(72) Inventors: Chunming Zhang, Midland, MI (US); Arvind Jaganathan, Midland, MI (US); Heqi Pan, Midland, MI (US); Philip Fontaine, Freeport, TX (US); Jerzy Klosin, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/574,051

(22) PCT Filed: May 27, 2016

(86) PCT No.: PCT/US2016/034666
§ 371 (c)(1),
(2) Date: Nov. 14, 2017

(87) PCT Pub. No.: WO2018/013067
PCT Pub. Date: Jan. 18, 2018

(65) Prior Publication Data
US 2018/0230099 A1  Aug. 16, 2018

Related U.S. Application Data

(60) Provisional application No. 62/167,852, filed on May 28, 2015.

(51) Int. Cl.
*C07D 209/86* (2006.01)
*C07D 209/88* (2006.01)
*C07F 7/08* (2006.01)

(52) U.S. Cl.
CPC ......... *C07D 209/86* (2013.01); *C07D 209/88* (2013.01); *C07F 7/083* (2013.01)

(58) Field of Classification Search
CPC ............................ C07D 209/86; C07D 209/88
USPC ........................................ 548/406, 440, 447
See application file for complete search history.

(56) References Cited

U.S. PATENT DOCUMENTS

| 6,900,215 | B2 * | 5/2005 | Chambers | C07D 487/04 |
| | | | | 514/259.1 |
| 7,053,255 | B2 * | 5/2006 | Ikeda | C07C 13/567 |
| | | | | 252/301.16 |
| 8,501,901 | B2 * | 8/2013 | Kitazawa | C08G 61/122 |
| | | | | 136/263 |

FOREIGN PATENT DOCUMENTS

WO  2012027448 A1  3/2012
WO  2014209927 A1  12/2014

OTHER PUBLICATIONS

Dwivedi et al., "A green protocol for the Pd catalyzed ligand free homocoupling reaction of arylboronic acids under ambient conditions", RSC Adv., 2014, 4, 41045-41050.
Kim et al., "A Tuned Bicyclic Proazaphosphatrane for Catalytically Enhanced N-Arylation Reactions with Aryl chlorides", Eur. J. Org. Chem., 2015, 1954-1960.
Kitawaki et al., "One-step construction of carbazoles by way of the palladiumcatalyzed double N-arylation reaction and its application to the total synthesis of murrastifoline-A", Tetrahedron, 2006, 62, 6792-6801.
Kuwahara et al., "Double N-Arylation of Primary Amines: Carbazole Synthesis from 2,2'-Biphenyldiols", Journal of Organic Chemistry (2005), 70(2), 413-419.

(Continued)

*Primary Examiner* — Nyeemah A Grazier
(74) *Attorney, Agent, or Firm* — Dinsmore & Shohl LLP

(57) ABSTRACT

A process for preparing one or more carbazoles comprising (a) contacting one or more compounds represented by formula (1) below with diboron reagents in the presence of PdCl2(dppf) to form one or more 2,2'-dichlorobiaryl represented by formula (2) below; and (b) contacting the one or more 2,2'-dichlorobiaryls with one or more H2N—Y compounds, in the presence of one or more palladium containing catalytic components; thereby forming one or more carbazoles represented by formula (3) below is provided.

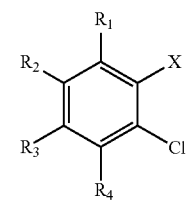

(1)

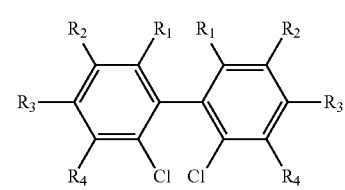

(2)

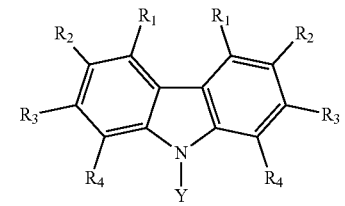

(3)

6 Claims, No Drawings

(56) References Cited

OTHER PUBLICATIONS

Kawaguchi et al., "Synthesis of Ladder-Type π-Conjugated Heteroacenes via Palladium-Catalyzed Double N-Arylation and Intramolecular O-Arylation", Journal of Organic Chemistry (2007), 72(14), 5119-5128.
Nozaki et al., "The Double N-Arylation of Primary Amines: Toward Multisubstituted Carbazoles with Unique Optical Properties", Angew. Chem. Int. Ed., 2003, 42, 2051-2053.
Zeng et al., "Palladium-Catalyzed Reductive Homocoupling of Aromatic Halides and Oxidation of Alcohols", J. Org. Chem., 2010, 75, 2556-2563.
Zhang et al., "Multicomponent Muiticatalyst Reactions (1111C)2R: One-Pot Synthesis of 3,4-Dihydroquinolinones", Organic Letters, 2013, 15, 2128-2131.
Zhou et al., "Highly Efficient Ligands for the Palladium-Assisted Double N-Arylation of Primary Amines for One-Sep Construction of Carbazoles", Adv. Synth. Catal., 2010, 352, 616-620.
International Search Report and Written Opinion pertaining to PCT/US2016/034666 dated Aug. 9, 2016.
International Preliminary Report on Patentability pertaining to PCT/US2016/034666 dated Jan. 9, 2018.

\* cited by examiner

PROCESS FOR PREPARING CARBAZOLES

FIELD OF DISCLOSURE

The disclosure relates to a process for preparing carbazoles.

BACKGROUND OF THE DISCLOSURE

Carbazoles are versatile synthetic building blocks with broad applications in advanced materials and medicinal chemistry. Preparation of carbazoles generally involve chemistries that are challenging to scale-up and inefficient. Such processes involve reactions such as aromatic nitration and harsh reductive cyclization and often employ expensive and/or materials which are not readily accessible. A process for preparing carbazoles using less expensive and readily available materials would be beneficial.

SUMMARY OF THE DISCLOSURE

The disclosure generally provides an efficient preparation of carbazoles from readily accessible, less expensive 2,2'-dichlorobiaryls via palladium-catalyzed double N-arylation of N-substituted amines.

In one embodiment, the disclosure provides a process for preparing one or more carbazoles comprising (a) contacting one or more compounds represented by formula (1) below

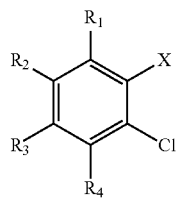

(1)

wherein Cl is a chlorine atom; X is selected from the group consisting of bromo, iodo, triflate (trifluoromethanesulfonate), mesylate (methanesulfonate), arenesulfonates such as tosylate (toluenesulfonate), and nonaflate (nonafluorobutanesulfonate); $R_1$-$R_4$ are selected from the group consisting of hydrogen alkyls, fluoroalkyls, aryls, heteroaryls, alkoxys, tertiary amines, fluoro, nitrile (CN), nitro ($NO_2$), and trialkyl(aryl)silyls, trialkyl(aryl)germanium and $R_1$-$R_4$ are never the same as X with diboron compounds selected from but not limited to bis(pinacolato)diboron, bis(catecholato)diboron, bis(hexyleneglycolato)diboron, bis(neopentylgycolato)diboron, 4,4,4',4',6,6,6',6'-octamethyl-2,2'-bi(1,3,2-dioxaborinane), tetrahydroxydiboron, 2,2'-bi(1,3,2-dioxaborinane) in the presence of a palladium (Pd) pre-catalyst or catalyst with or without a ligand to form one or more 2,2'-dichlorobiaryl represented by formula (2);

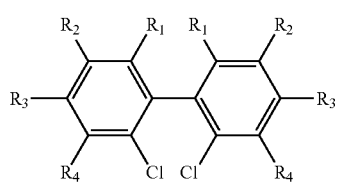

(2)

the Pd pre-catalyst or catalyst is chosen from palladium (II) acetate (Pd(OAc)$_2$), palladium chloride (PdCl$_2$), tris(dibenzylideneacetone)dipalladium(0) (Pd$_2$(dba)$_3$), bis(triphenylphosphine)palladium(II) dichloride (PdCl$_2$(PPh$_3$)$_2$), bis(triphenylphosphine)palladium (II) acetate (Pd(OAc)$_2$(PPh$_3$)$_2$) and (1,1'-bis(diphenylphosphino)ferrocene)dichloropalladium (II) (PdCl$_2$(dppf)), (1,1'-bis(diphenylphosphino)ferrocene)dichloropalladium (II) complex with dichloromethane (PdCl$_2$(dppf)CH2Cl$_2$), and the ligand is selected from phosphine ligands such as 1,1'-bis(diphenylphosphino)ferrocene (dppf), tri(o-totyl)phosphine ("(o-tol)$_3$P") and rac-2,2'-bis(diphenylphosphino)-1,1'-binaphthyl ("rac-BINAP") and (b) contacting the one or more 2,2'-dichlorobiaryls represented by formula (2) with one or more ammonia derivative of the general formula H$_2$N—Y, wherein Y is selected from the group consisting of H, —CH$_2$Ar, —COOR, —C(O)R, SiR$_3$, SiAr$_3$, Na, Li, and, 2-pyrimidyl, wherein Ar is an aryl group such as phenyl, substituted phenyl and napthyl group and R is selected from the group consisting of alkyls, aryls, heteroaryls, and alkoxys in the presence of one or more palladium containing catalytic components;

thereby forming one or more carbazoles represented by formula (3) below

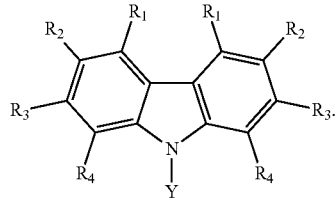

(3)

DETAILED DESCRIPTION OF THE DISCLOSURE

As used herein, biaryl refers to a compound containing a substructure comprising two aromatic rings, i.e. aryl groups, joined by one single bond. The aryl groups are aromatic groups having from 6 to 24 carbon atoms. A 2,2'-dichlorobiaryl represented by formula (2) is any biaryl compound wherein each aromatic ring has one chlorine atom substituted for a hydrogen atom at the 2 and 2' position, which is prepared from one or more compounds represented by formula (1). The aromatic rings of the 2,2'-dichlorobiaryls may, in some embodiments, further include additional substituent groups in addition to the chlorine atoms.

In the first step in the process of the present disclosure a diboron compound selected from but not limited to bis(pinacolato)diboron, bis(catecholato)diboron, bis(hexyleneglycolato)diboron, bis(neopentylgycolato)diboron, 4,4,4',4',6,6,6',6'-octamethyl-2,2'-bi(1,3,2-dioxaborinane), tetrahydroxydiboron, 2,2'-bi(1,3,2-dioxaborinane) is contacted with one or more compounds represented by formula (1) below

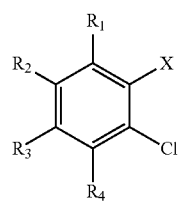

(1)

wherein Cl is a chlorine atom; X is selected from the group consisting of bromo, iodo, triflate (trifluoromethanesulfonate), mesylate (methanesulfonate), arenesulfonates such as tosylate (toluenesulfonate), and nonaflate (nonafluorobutanesulfonate) and $R_1$-$R_4$ are selected from the group consisting of substituted and unsubstituted hydrogen alkyl, cycloalkyl, fluoroalkyl, aryl, heteroaryl, alkoxy, tertiary amines, fluoro, nitrile (CN), nitro (NO2)trialkyl(aryl)silyl, and trialkyl(aryl)germanium.

As used herein, the term "alkyl" is a hydrocarbyl wherein the hydrocarbon radical is non-aromatic, saturated, straight chain or branched, acyclic, and unsubstituted or substituted.

Preferably, each alkyl independently has a maximum of 40, more preferably 20, still more preferably 12, and still more preferably 8 carbon atoms. Examples of unsubstituted (C1-C40)alkyl are unsubstituted (C1-C20)alkyl; unsubstituted (C1-C10)alkyl; unsubstituted (C1-C5)alkyl; methyl; ethyl; 1-propyl; 2-propyl; 1-butyl; 2-butyl; 2-methylpropyl; 1,1-dimethylethyl; 1-pentyl; 1-hexyl; 1-heptyl; 1-octyl, (2,2,4,4-tetramethyl)pentyl, 1-nonyl; and 1-decyl. Examples of substituted (C1-C40)alkyl are substituted (C1-C20)alkyl, substituted (C1-C10)alkyl, trifluoromethyl, and (C45)alkyl. The (C45)alkyl is, for example, a (C27-C40)alkyl substituted by one $R^S$, which is a (C18-C5)alkyl, respectively. Preferably, each (C1-C5)alkyl independently is methyl, trifluoromethyl, ethyl, 1-propyl, 2-methylethyl, or 1,1-dimethylethyl.

Each fluoroalkyl group can include one or more fluorine atoms, for example, a single fluorine atom, two fluorine atoms (e.g., as a 1,1-difluoroethyl group), three fluorine atoms (e.g., as a 2,2,2-trifluoroethyl group), or fluorine atoms at each free valence of carbon (e.g., as a perfluorinated group such as —$CF_3$, —$C_2F_5$, —$C_3F_7$, or —$C_4F_9$).

Preferably, each aryl independently has from 6 to 40 carbon atoms. The term "(C6-C40)aryl" means an unsubstituted or substituted (by at least one $R^S$) mono-, bi- or tricyclic aromatic hydrocarbon radical of from 6 to 40, preferably from 6 to 14, ring carbon atoms, and the mono-, bi- or tricyclic radical comprises 1, 2 or 3 rings, respectively, wherein the 1 ring is aromatic; at least one of the 2 or 3 rings is aromatic; and the 2 or 3 rings independently are fused or non-fused. Other aryl groups (e.g., (C6-C.10)aryl)) are defined in an analogous manner. Preferably, (C6-C40)aryl has a maximum of 20 carbon atoms (i.e., (C6-C20)aryl), more preferably 18 carbon atoms, still more preferably 10 carbon atoms, and even more preferably 6 carbon atoms. Examples of unsubstituted (C6-C40)aryl are unsubstituted (C6-C20)aryl; unsubstituted (C6-C18)aryl; phenyl; (C3-C6) cycloalkyl-phenyl; fluorenyl; tetrahydrofluorenyl; indacenyl; hexahydroindacenyl; indenyl; dihydroindenyl; naphthyl; tetrahydronaphthyl; and phenanthrene. Examples of substituted (C6-C40)aryl are substituted (C6-C20)aryl; substituted (C6-C18)aryl; 2-(C1-5)alkyl-phenyl; 2,4-bis(C1-5) alkyl-phenyl; 2,4-bis[(C20)alkyl]-phenyl; polyfluorophenyl; pentafluorophenyl; and fluoren-9-one-1-yl.

Preferably, each cycloalkyl independently has from 3 to 40 carbon atoms. The term "(C3-C40)cycloalkyl" means a saturated cyclic hydrocarbon radical of from 3 to 40 carbon atoms that is unsubstituted or substituted by at least one $R^S$. Other cycloalkyl groups (e.g., (C3-C12)alkyl)) are defined in an analogous manner. Preferably, (C3-C40)cycloalkyl has a maximum of 20 carbon atoms (i.e., (C3-C30)cycloalkyl), more preferably 10 carbon atoms, and still more preferably 6 carbon atoms. Examples of unsubstituted (C3-C40)cycloalkyl are unsubstituted (C3-C20)cycloalkyl, unsubstituted (C3-C10)cycloalkyl, cyclopropyl, cyclobutyl, cyclopentyl, cyclohexyl, cycloheptyl, cyclooctyl, cyclononyl, and cyclodecyl. Examples of substituted (C3-C40)cycloalkyl are substituted (C3-C20)cycloalkyl, substituted (C3-C10)cycloalkyl, cyclopentanon-2-yl, and 1-fluorocyclohexyl.

Aryl groups useful as substituent groups include phenyl, naphthyl, thienyl, indolyl, xylyl and tolyl groups, preferably phenyl group Preferably, each heteroaryl independently has from 1 to 40 carbon atoms. The term "(C1-C40)heteroaryl" means an unsubstituted or substituted (by at least one $R^S$) mono-, bi- or tricyclic heteroaromatic hydrocarbon radical of from 3 to 20 total carbon atoms and from 1 to 4 heteroatoms; from 1 to 44 total ring atoms, preferably from 5 to 10 total ring atoms, and the mono-, bi- or tricyclic radical comprises 1, 2 or 3 rings, respectively, wherein the 1-ring is heteroaromatic; at least one of the 2 or 3 rings is heteroaromatic; and the 2 or 3 rings independently are fused or non-fused. Other heteroaryl groups (e.g., (C1-C12)heteroaryl)) are defined in an analogous manner. The monocyclic heteroaromatic hydrocarbon radical is a 5-membered or 6-membered ring. The 5-membered ring has from 1 to 4 carbon atoms and from 4 to 1 heteroatoms, respectively, each heteroatom being O, S, N, or P, and preferably O, S, or N. Examples of 5-membered ring heteroaromatic hydrocarbon radical are pyrrol-1-yl; pyrrol-2-yl; furan-3-yl; thiophen-2-yl; pyrazol-1-yl; isoxazol-2-yl; isothiazol-5-yl; imidazol-2-yl; oxazol-4-yl; thiazol-2-yl; 1,2,4-triazol-1-yl; 1,3,4-oxadiazol-2-yl; 1,3,4-thiadiazol-2-yl; tetrazol-1-yl; tetrazol-2-yl; and tetrazol-5-yl. The 6-membered ring has 4 or 5 carbon atoms and 2 or 1 heteroatoms, the heteroatoms being N or P, and preferably N. Examples of 6-membered ring heteroaromatic hydrocarbon radical are pyridine-2-yl; pyrimidin-2-yl; and pyrazin-2-yl. The bicyclic heteroaromatic hydrocarbon radical preferably is a fused 5,6- or 6,6-ring system. Examples of the fused 5,6-ring system bicyclic heteroaromatic hydrocarbon radical are indol-1-yl; and benzimidazole-1-yl. Examples of the fused 6,6-ring system bicyclic heteroaromatic hydrocarbon radical are quinolin-2-yl; and isoquinolin-1-yl. The tricyclic heteroaromatic hydrocarbon radical preferably is a fused 5,6,5-; 5,6,6-; 6,5,6-; or 6,6,6-ring system. An example of the fused 5,6,5-ring system is 1,7-dihydropyrrolo[3,2-f] indol-1-yl. An example of the fused 5,6,6-ring system is 1H-benzo[f]indol-1-yl. An example of the fused 6,5,6-ring system is 9H-carbazol-9-yl, which may also be named as a dibenzo-1H-pyrrole-1-yl. An example of the fused 6,5,6-ring system is 9H-carbazol-9-yl. An example of the fused 6,6,6-ring system is acrydin-9-yl. The 5-membered rings and 6-membered rings of the fused 5,6-; 6,6-; 5,6,5-; 5,6,6-; 6,5,6-; and 6,6,6-ring systems independently can be as described above for 5-membered and 6-membered rings, respectively, except where the ring fusions occur.

Alkoxy groups may be selected from the group consisting of methoxy, ethoxy, isopropoxy, butoxy and pentoxy groups.

Exemplary tertiary amine substituents include dialkyl amines where the alkyl group is selected from C1-C40 alkyls.

Exemplary silyl groups could include trimethylsilyl, triethylsilyl, triiosoprpylsilyl, dimethyl-octylsilyl, dimethyl-decylsilyl, diisopropyl-octylsilyl, and combinations thereof.

None of $R_1$, $R_2$, $R_3$ and $R_4$ are the same as X.

The contacting of the compound of formula (1) with diboron reagents selected from but not limited to bis(pinacolato)diboron, bis(catecholato)diboron, bis(hexyleneglycolato)diboron, bis(neopentylgycolato)diboron, 4,4,4',4',6,6,6',6'-octamethyl-2,2'-bi(1,3,2-dioxaborinane), tetrahydroxydiboron, 2,2'-bi(1,3,2-dioxaborinane) occurs in the presence of $PdCl_2$((diphenylphosphino)ferrocene), "PdCl$_2$(dppf)," to form one or more 2,2'-dichlorobiaryl compounds represented by formula (2).
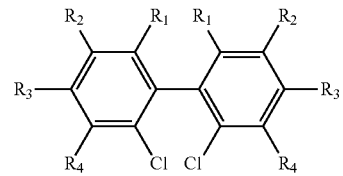
Exemplary dichlorobiaryl compounds which may be made in the first step of the process include:
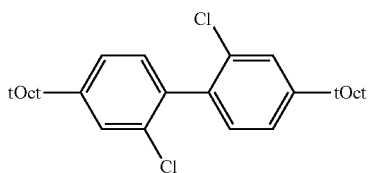
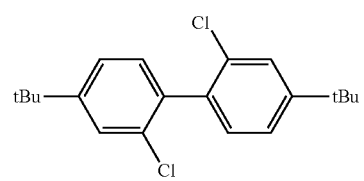
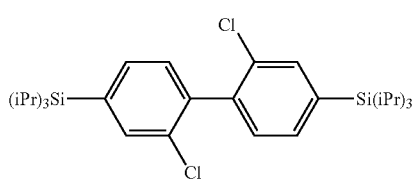
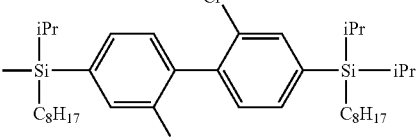
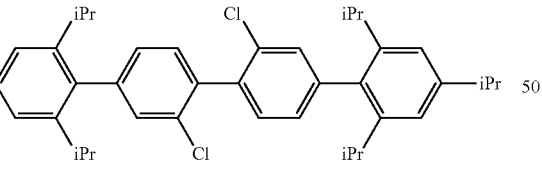
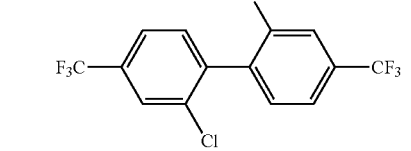
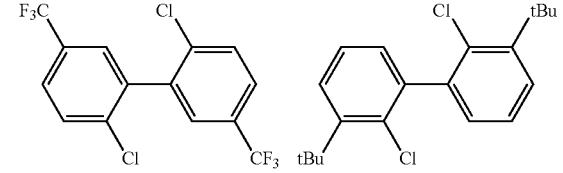
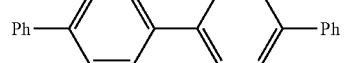
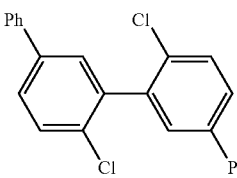
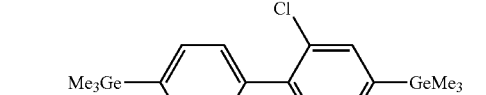

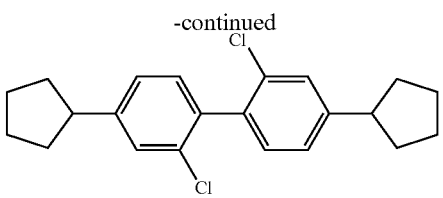

In a second step of the process according to the disclosure, the one or more dichlorobiaryls are contacted with one or more H₂N—Y compounds, wherein Y is selected from the group consisting of H, —COOR, —C(O)R, SiR₃, SiAr₃, CH₂Ar, Na, Li, and pyrimidin-2-yl, wherein Ar is a aryl group and R is selected from the group consisting of alkyls, aryls, heteroaryls, and alkoxys in the presence of one or more palladium containing catalytic components.

As used herein, the term palladium containing catalytic components includes both palladium containing catalysts as well as a palladium containing precursor in conjunction with or without a phosphine ligand. Exemplary palladium containing precursors include palladium acetate (Pd(OAc)₂), PdCl₂, Pd₂(dba)₃, PdCl₂ (PPh₃)₂, Pd(OAc)₂(PPh₃)₂ and PdCl₂(dppf), PdCl2(dppf)CH₂Cl₂. Exemplary phosphine ligands include tertiary phosphines which include phosphines containing (cyclo)alkyl and/or aryl groups. Examples of suitable trialkyl phosphines are triethyl phosphine, tri-n-butyl phosphine, tri-isobutyl phosphine, tripentyl phosphine, trihexyl phosphine, trioctyl phosphine, trilauryl phosphine, lauryl dimethyl phosphine, hexyl dipropyl phosphine and ethyl butyl octyl phosphine. Examples of suitable phosphines containing one or more aromatic groups or cycloalkyl groups are tricyclohexyl phosphine, triphenyl phosphine, tri(o-totyl)phosphine, tri(p-tolyl) phosphine, dimethyl phenyl phosphine, methyl diphenyl phosphine, tri(m-ethylphenyl) phosphine and tri(2,4-dimethyl phenyl) phosphine. A suitable diphosphine which may be used is bis(diphenyl phosphine)-ethane or dppf. Also the arsine and antimony homologs may be advantageously used. The above-mentioned ligand compounds may further be substituted by halogen atoms, such as chlorine atoms, nitrile and/or nitro groups and the like. Also ligand compounds which contain in addition hydrophilic groups, such as —COOM, —SO₃M, and/or —NH2 groups attached directly or via an alkylene group to the phosphine substituent(s), may be used. In the above-mentioned groups M represents an inorganic or organic cationic residue, such as an alkali or alkaline earth metal cation or a quaternary ammonium ion.

The process of the present disclosure results in the formation of one or more carbazoles represented by formula (3) below

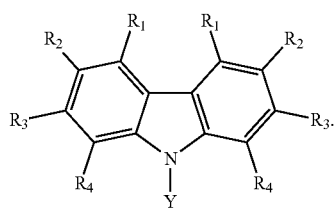

(3)

Exemplary carbazoles which may be formed by the process include but not limited to:

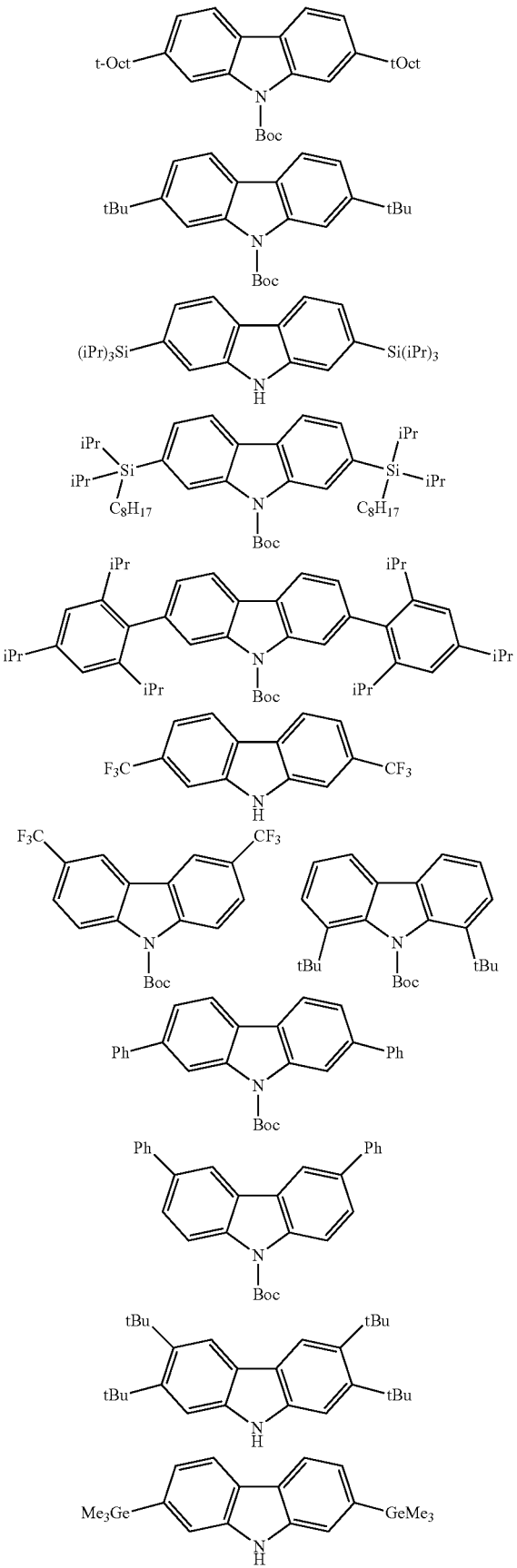

-continued

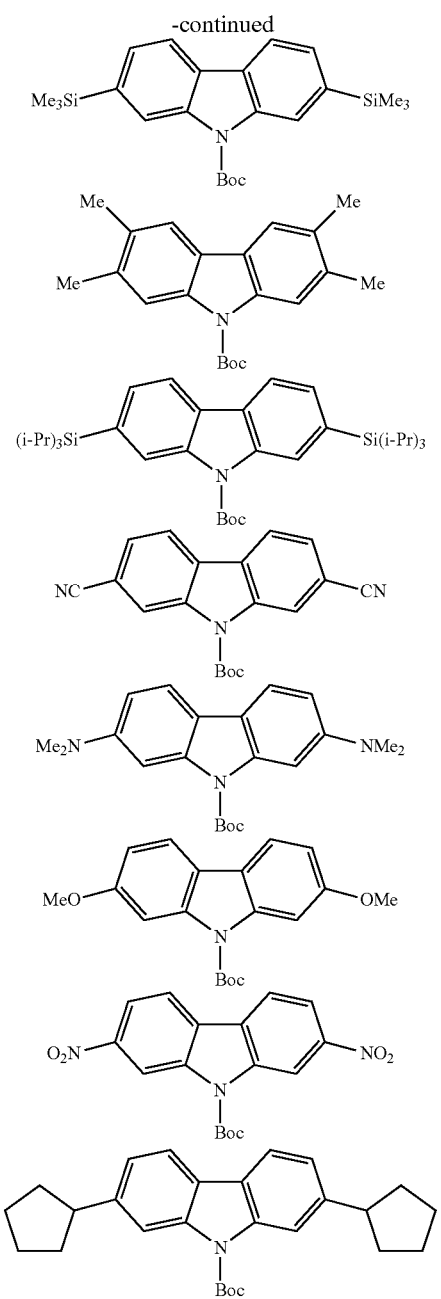

In an alternative embodiment, the disclosure provides the process according to any embodiment disclosed herein, except that Y is tert-butyloxycarbonyl (Boc).

In an alternative embodiment, the disclosure provides the process according to any embodiment disclosed herein, except that the one or more compounds represented by formula (1) comprise 2-chloro-4-substituted phenyl trifluoromethanesulfonate.

In an alternative embodiment, the disclosure provides the process according to any embodiment disclosed herein, except that the one or more compounds represented by formula (1) comprises 2-chloro-4-tert-octylphenyl trifluoromethanesulfonate.

In an alternative embodiment, the disclosure provides the process according to any embodiment disclosed herein, except that the one or more carbazoles comprises tert-butyl 2,7-di-tert-octyl-9H-carbazole-9-carboxylate.

In an alternative embodiment, the disclosure provides the process according to any embodiment disclosed herein, except that the one or more carbazoles are selected from the group consisting of 2,7-disubstituted carbazoles, -1,8-disubstituted carbazoles; 3,6-disubstituted carbazoles, and 4,5-disubstituted carbazoles.

EXAMPLES

The following examples illustrate the present invention but are not intended to limit the scope of the invention.

Synthesis of tert-butyl
2,7-di-tert-octyl-9H-carbazole-9-carboxylate

1. Preparation of 2,2'-dichloroaryl: 2,2'-dichloro-4,
4'-di-tert-octylbiphenyl

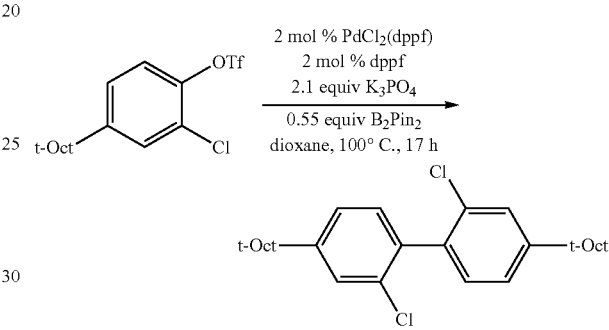

wherein OTf means triflate (trifluoromethanesulfonate); t-Oct means a 2,2,4,4-tetramethylpentyl; and $B_2Pin_2$ means bis(pinacolato)diboron.

A 3-neck reaction vessel equipped with a magnetic stir bar, $N_2$ inlet, a reflux condenser and a /septum is charged with the 2-chloro-4-tert-octylphenyl trifluoromethanesulfonate (56 g, 150 mmol, prepared from 2-chloro-4-tert-octylphenol), $B_2Pin_2$ (20 g, 78.8 mmol), $PdCl_2(dppf)$ (2.45 g, 3 mmol, 2 mol % with respect to triflate), dppf (1.66 g, 3.0 mmol, 3%), $K_3PO_4$ (67 g, 315 mmol, 2.1 eq), and degassed dioxane (200 mL) under nitrogen. The resulting suspension is purged with $N_2$ for 10-30 min at ambient temperature and then heated with stirring at 100° C. overnight (17 h). The reaction is cooled to ambient temperature and then diluted with water (100 mL) and heptane (50 mL). The aqueous and organic layers are separated. The aqueous layer is extracted with heptane (2×50 mL). The combined organic layer is washed with brine (1×50 mL) and then concentrated under reduced pressure. The dark brown residue is dissolved in heptane (50 mL) and then filtered through a pad of silica gel (7 cm width×5 cm height) eluting with heptane (400 mL). The slightly yellow filtrate is concentrated under reduced pressure to afford the crude product as a viscous yellow oil (33.3 g, 99% crude yield). A small seed crystal is added to the crude product and left in the refrigerator overnight. The resulting solid is filtered. The crude product thus obtained is pure enough for the use in the next step for preparation of the carbazole. Further purification may be accomplished by recrystallization from acetonitrile to a colorless solid. As an example, 1 g of the crude product is mixed with 2 mL of acetonitrile at 50° C. After cooling to room temperature, the product precipitates out as an oil, which gradually solidifies. The solids are filtered and dried to afford 800 mg of pure product as a colorless solid.

2. Preparation of Carbazole: tert-butyl 2,7-di-tert-octyl-9H-carbazole-9-carboxylate

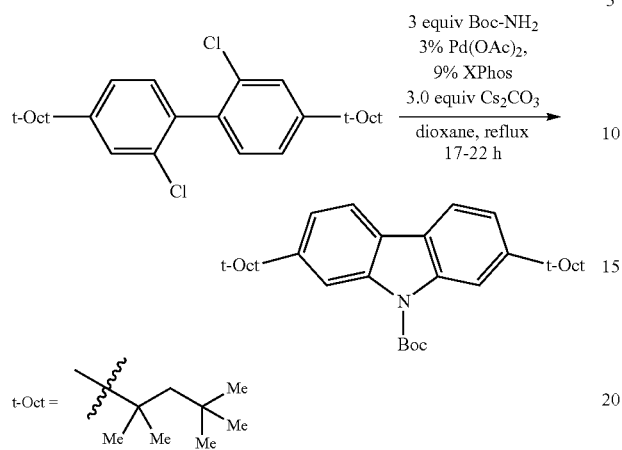

wherein BOC means tert-butyloxycarbonyl, XPhos means 2,-dicyclohexylphosphino-2',4',6'-triisopropylbiphenyl.

A 3-neck reaction vessel equipped with a reflux condenser, $N_2$ inlet, rubber septum, a thermometer and a stir bar is charged with $Pd(OAc)_2$ (75 mg, 3 mol %), 2-dicyclohexylphosphino-2',4',6'-triisopropylbiphenyl ("XPhos") (479 mg, 9 mol %) and degassed 1,4-dioxane (25 mL) under nitrogen. The resulting suspension is stirred for ~20 min with constant $N_2$ purge to ensure that the Xphos ligand is completely dissolved. The resulting clear, dark purple solution is then diluted with an additional 50 mL of degassed 1,4-dioxane. A solid mixture of t-butylcarbamate (3.9 g, 33.5 mmol, 3.0 equiv), $Cs_2CO_3$ (10.9 g, 3.0 equiv) and the biphenyl compound (5.0 g, 11.2 mmol, 1.0 equiv) is then added into the reaction vessel in a single portion. $N_2$ is purged through this stirred mixture for ~15 min. The reaction is then heated to 100° C. under $N_2$ until the reaction is complete (22 h) as monitored by periodic GC-MS analysis. The resulting mixture is cooled to ambient temperature and the volatiles are removed under reduced pressure. The crude residue is partitioned between water (100 mL) and EtOAc (100 mL). The aqueous layer is extracted with EtOAc (50 mL×2). The combined organics are washed with brine, concentrated and passed through a pad of silica gel (~5 cm×5 cm; 5% EtOAc in hexanes as eluent). The filtrate is concentrated to give the crude product (5.7 g) as an off white solid contaminated with a trace amount of Xphos ligand). Further purification may be accomplished by recrystallization from hexane or heptane in 92% yield.

TEST METHODS

Test methods include the following:
GC-MS and NMR spectra. GC samples were analyzed on an Agilent Technologies 6890 GC system using a J&W DB-5 capillary column with 15-m×0.32 ID and 0.25-μm thick film. The GC temperature program was: 80° C. for 2 min, then ramp to 250° C. at 20° C./min, then hold at 250° C. for 15 min. Mass spectra (MS) data was obtained using an Agilrnt Technologies Inert Mass Selective Detector (70eV, EI).
$^1H$ and $^{13}C$ NMR analysis was used to confirm the identity of the product. $^1H$ and $^{13}C$ NMR spectra were recorded on a Bruker 400 (FT 400 MHz, 1H; 101 MHz, 13C) spectrometer.

We claim:
1. A process for preparing a carbazole comprising:
(a) contacting a compound represented by formula (1) below

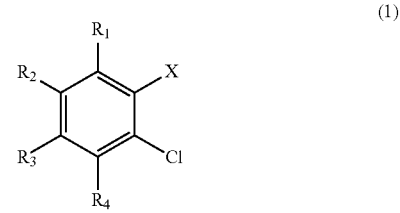

wherein Cl is a chlorine atom; X is selected from the group consisting of bromo, iodo, triflate (trifluoromethanesulfonate), mesylate (methanesulfonate), arenesulfonates; $R_1$-$R_4$ are selected from the group consisting of hydrogen, alkyls, fluoroalkyls, aryls, heteroaryls, alkoxys, tertiary amines, fluoro, nitrile (CN), nitro ($NO_2$), and trialkyl(aryl) silyl; and $R_1$-$R_4$ are never the same as X with diboron reagents in the presence of $PdCl_2$(dppf) to form a dichlorobiaryl represented by formula (2);

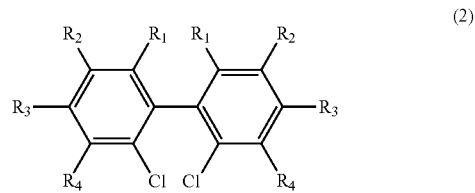

and (b) contacting the 2,2'-dichlorobiaryl represented by formula (2) with a $H_2N$—Y compound, wherein Y is selected from the group consisting of H, —COOR, —C(O)R, $SiR_3$, $SiAr_3$, $CH_2Ar$, Na, Li, and 2-pyrimidyl, wherein Ar is a phenyl group and R is selected from the group consisting of alkyls, aryls, heteroaryls, and alkoxys in the presence of palladium containing catalytic components;
thereby forming the carbazole represented by formula (3) below

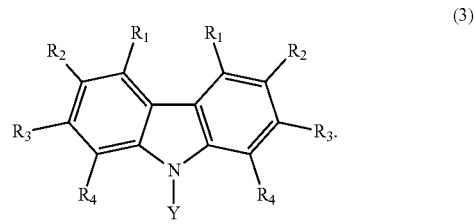

2. The process according to claim 1 wherein Y is tert-butyloxycarbonyl, or H.
3. The process according to claim 1, wherein the compound represented by formula (1) comprises 2-chloro-4--substituted phenyl trifluoromethanesulfonate where the substituent may be a alkyl, silyl, tertiary amines, or alkoxy.
4. The process according to claim 1, wherein the compound represented by formula (1) comprises 2-chloro-4-tert-octylphenyl trifluoromethanesulfonate.

5. The process according to claim 1, wherein the carbazole comprises tert-butyl 2,7-di-tert-octyl-9H-carbazole-9-carboxylate.

6. The process according to claim 1, wherein the carbazole is selected from the group consisting of 2,7-disubstituted carbazoles, -1,8-disubstituted carbazoles; 3,6-disubstituted carbazoles, and 4,5-disubstituted carbazoles.

* * * * *